US00PP37421P2

(12) United States Plant Patent
Kordes

(10) Patent No.: US PP37,421 P2
(45) Date of Patent: May 12, 2026

(54) MINIATURE ROSE PLANT NAMED 'KORpot139'

(50) Latin Name: *Rosa hybrida*
Varietal Denomination: KORpot139

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/375,332

(22) Filed: Oct. 31, 2025

(51) Int. Cl.
*A01H 5/02* (2018.01)
*A01H 6/74* (2018.01)

(52) U.S. Cl.
USPC ..... Plt./127

(58) Field of Classification Search
USPC ..... Plt./101, 116, 127
See application file for complete search history.

(56) References Cited

U.S. PATENT DOCUMENTS

PP24,207 P2 * 2/2014 Kordes ..... A01H 5/02 Plt./101
PP30,845 P3 8/2019 Kordes
PP36,955 P3 9/2025 Kordes

* cited by examiner

*Primary Examiner* — Susan Mccormick Ewoldt
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot139', is described. The new plant variety forms in abundance on a substantially continuous basis coral-orange-colored blossoms. The growth habit is compact. Semi-glossy, medium green foliage is formed. Additionally, the new plant variety is particularly well suited for growing as distinctive ornamentation in the landscape.

1 Drawing Sheet

Latin name of genus and species of plant claimed: *Rosa hybrida.*

Variety denomination: 'KORpot139'.

STATEMENT REGARDING PRIOR DISCLOSURES BY THE INVENTOR

The first sale or offer for sale of the new plant variety was November 2024 on the *ROSA* DANICA website. The first sale or offer for sale of the new plant variety was by the inventor or another who obtained the new plant variety directly or indirectly from the inventor. No plants of the new plant variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of Miniature rose plant of the present invention was discovered as a branch mutation of the 'KORpot126' variety (U.S. Plant Pat. No. 36,955) in March 2024 in Offenseth-Sparrieshoop, Germany. It was first propagated in April 2024 from the parent plant.

The new plant variety has been found to undergo asexual propagation in Klein Offenseth-Sparrieshoop by a number of routes such as vegetative cuttings. Asexual propagation techniques in Klein Offenseth-Sparrieshoop, such as vegetative cuttings, have shown that the characteristics of the new plant variety are homogeneous, stable, and strictly transmissible by such asexual propagation from one generation to another. Accordingly, the new plant variety undergoes asexual propagation in a true-to-type manner.

SUMMARY OF THE INVENTION

It was found that the new variety of miniature rose plant of the present invention possesses the following combination of characteristics:

(a) abundantly and substantially continuously forming coral-orange-colored blossoms,
(b) exhibiting a compact growth habit, and
(c) forming semi-glossy, medium green foliage.

The new plant variety well meets the needs of the horticultural industry. It can be grown to advantage as distinctive ornamentation in parks, gardens, public areas, and residential landscapes. Accordingly, it is particularly well suited for growing in the landscape.

The new plant variety can be readily distinguished from its ancestors. More specifically, the new plant variety displays a more compact growth habit, and a larger flower size compared to the parental 'KORpot126' variety and the new plant variety produces coral-orange-colored blossoms, whereas the 'KORpot126' variety produces yellow-colored blossoms. Moreover, the new plant variety can be readily distinguished from non-parental related similar varieties. For example, the new plant variety displays coral-orange-colored blossoms and has a shorter flower duration on the plant compared to the 'KORpot080' variety (U.S. Plant Pat. No. 30,845), which displays dark yellow-colored-blossoms.

The new variety has been named the 'KORpot139' variety.

BRIEF DESCRIPTION OF THE PHOTOGRAPH

The accompanying photograph shows, as nearly true as it is reasonably possible to make the same in a color illustration of this character, a typical specimen of the new plant variety and blossoms of the new plant variety. The illustrated rose plant of the new variety was approximately sixteen weeks of age and was grown indoors on its own roots in a 10.5 cm container in in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designations used herein represent the closest color observed on the majority of the specified botanical features. The description is based on a one-year-old specimen of the new plant variety which has been freshly shifted up from a 4-inch pot to growing in a 3-gallon container growing on its own roots in a greenhouse in Cochranville, Pennsylvania, observed during August 2025.

Botanical classification: *Rosa hybrida* cultivar 'KORpot139'.

Commercial classification: Miniature Rose.

Plant:

*Habit*.—Compact.

*Height*.—Approximately 10.0 cm on average from the top of the soil plane.

*Width*.—Approximately 10.0 cm on average.

Branches:

*Stem color*.—Old wood: Yellow-Green Group 144A. — young stems: Yellow-Green Group 144A.

*Length*.—Main stems: approximately 10.0 cm on average. — secondary stems: approximately 5.0 cm on average.

*Diameter*.—Main stems: approximately 3.0 mm on average. — secondary stems: approximately 1.5 mm on average.

*Texture*.—Smooth.

*Prickles*.—Amount: medium; 4 to 5 prickles per internode. — young prickles: length is approximately 4.0 mm on average; width is approximately 1.0 mm on average at point of attachment; and color is Greyed-Orange Group 164B. — old prickles: length is approximately 5.0 mm on average; width is approximately 2.0 mm on average at point of attachment; and color is Greyed-Orange Group 165A.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 3.1 cm on average; width is approximately 1.8 cm on average. — lower leaflets: length is typically 1.5 cm to 2.1 cm; width is typically 7.0 mm to 1.3 cm. — 5-Leaflet leaf. length is approximately 6.8 cm on average; width is approximately 4.5 cm on average.

Foliage:

*Young foliage*.—Upper surface color: Yellow-Green Group 147A with indistinguishable venation. — under surface color: Yellow-Green Group 147B with indistinguishable venation.

*Old foliage*.—Upper surface color: Green Group NN137A with indistinguishable venation. — under surface color: Green Group NN137C with indistinguishable venation.

*Petiole*.—Texture: upper surface is hispid; under surface is hispid. — length: approximately 1.3 cm on average. — width: approximately 1.0 mm on average. — upper surface color: Green Group 143A. — under surface color: Yellow-Green Group 144A.

*Rachis*.—Length: approximately 1.3 cm on average. — width: approximately 1.0 mm on average. — upper surface color: Green Group 143A. — under surface color: Yellow-Green Group 144A.

*Stipules*.—Length: approximately 5.0 mm on average. — width: approximately 1.0 mm on average. — margin: entire to erose. — upper surface color: Green Group 143A. — lower surface color: Yellow-Green Group 144A.

Inflorescence:

*Number of flowers*.—About 10 to 15 blooms on average on a plant at once.

*Number of blossoms per stem or in a cluster*.—Typically between 1 and 3 blooms per stem on average.

*Peduncle*.—Color: Yellow-Green Group 144A. — diameter: approximately 2.0 mm on average. — length: approximately 2.5 cm on average. — surface texture: hispid.

*Sepals*.—Number: 5. — upper surface color and texture: Green Group 138B, puberulent. — under surface color and texture: Yellow-Green Group 144A, covered in short pubescence. — size: length is approximately 1.8 cm on average; width is approximately 6.0 mm on average. — margin: entire with extensions on most sepals measuring approximately 1.0 mm in length and 1.0 mm in width on average. — shape: lanceolate. — apex: acute to aristate. — base: truncate as it joins the receptacle.

*Buds*.—Shape: ovoid. — size: length is approximately 1.8 cm on average; width is approximately 6.0 mm on average. — color (when opening): Red Group 39B.

*Flower*.—Form: double, cuplike. — profile: concave as it opens, and then outer petals are convex as the bloom ages and opens further. — diameter: approximately 5.0 cm on average. — height: approximately 2.0 cm on average. — duration: on the plant approximately 10 to 12 days. — petal color when first and fully opened: upper surface is equally Red Group 39B and Red Group 39C, randomly streaked with Red Group 39B and Red Group 39C with a large basal spot of Yellow Group 9B; under surface is equally Red Group 39B and Red Group 39C, randomly streaked with Red Group 39B and Red Group 39C with a large basal spot of Yellow Group 9B. — petal color at end of bloom: upper surface is Yellow Group 10C with a small basal spot of Yellow Group 10A; under surface is Yellow Group 10C with a small basal spot of Yellow Group 10A. — petals reflex one by one: yes.

*Fragrance*.—Very slight to no noticeable scent.

*Petal*.—Number: 15 to 20 on average. — drop: average. — length: approximately 2.4 cm on average. — width: approximately 2.0 cm on average. — overall shape: broadly obovate. — margin: entire with moderate undulation. — apex shape: rounded to slightly reniform. — base shape: cuneate. — texture: upper surface is smooth; under surface is smooth.

*Petaloids*.—Number: approximately 4 on average. — length: approximately 1.0 cm on average. — width: approximately 2.0 mm on average. — color: upper surface is Red Group 39B with a basal spot of Yellow Group 10A; under surface is Red Group 39B with a basal spot of Yellow Group 10A. — texture: upper surface is smooth; under surface is smooth. — margin: entire with moderate undulation. — shape: obovate. — apex: obovate. — base: linear.

*Stamen*.—Number: approximately 106. — anthers: number is approximately 106; color is Greyed-Orange Group 166A; length is approximately 1.0 mm on average; and shape is oval. — filaments: length is approximately 6.0 mm on average and color is Greyed-Orange Group 163B.

*Pistils*.—Arrangement: separate. — number: approximately 48.— style: length is approximately 6.0 mm on average and color is Yellow-Orange Group 16A. — stigma: diameter is approximately 1.0 mm on average; shape is fan shaped; color is Yellow-Orange Group 16B.

*Receptacle*.—Diameter: approximately 5.0 mm on average. — depth: approximately 7.0 mm on average. — shape: urn shaped. — color: Yellow-Green Group 144A. — surface texture: covered in short pubescence.

*Pollen*.—Amount: none observed.

*Hips/seed*.—None observed.

Development:

*Vegetation*.—Semi-glossy, medium green.

*Blossoming*.—Abundant and continuous from Spring through Fall in the greenhouse; typically, in bloom outdoors from May to November in Southeastern Pennsylvania.

*Resistance to diseases*.—Good resistance to powdery mildew (*Podosphaera pannosa*).

*Hardiness*.—Unknown.

The new 'KORpot139' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot139' characterized by the following combination of characteristics:

(a) abundantly and substantially continuously forming coral-orange-colored blossoms, (b) exhibiting a compact growth habit, and (c) forming semi-glossy, medium green foliage;

substantially as herein shown and described.

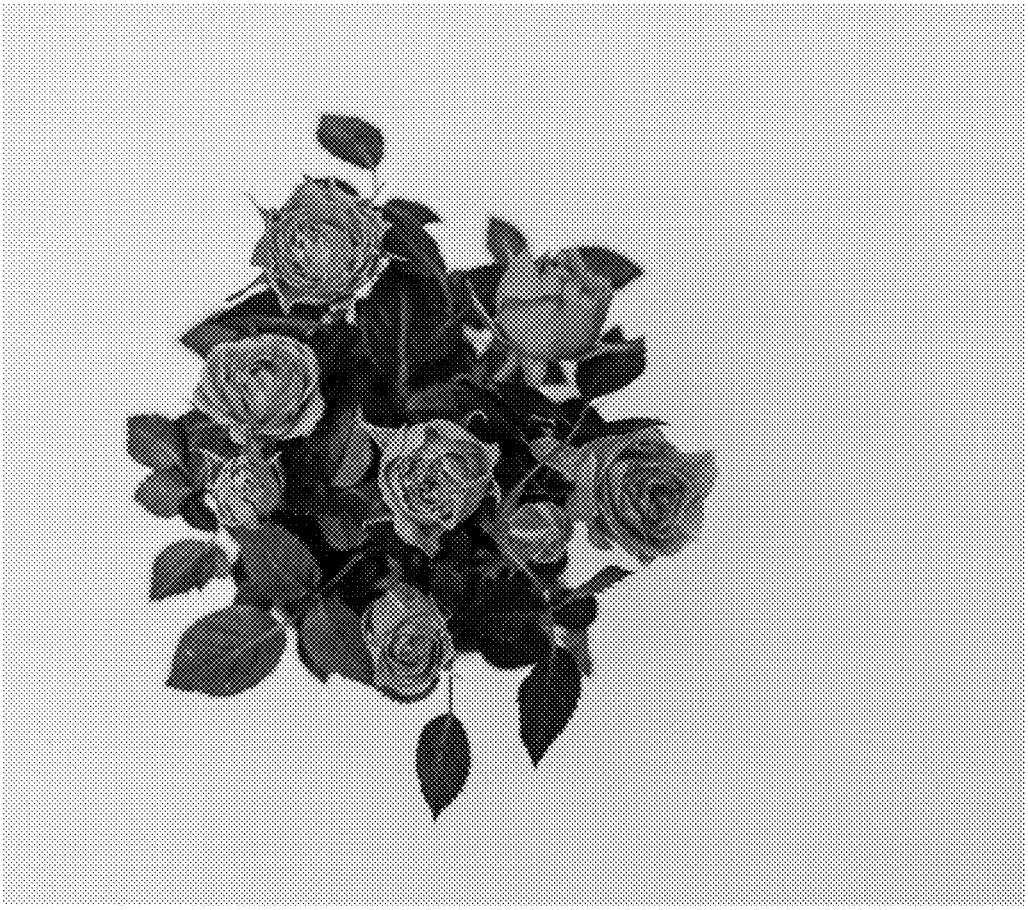

* * * * *